(12) United States Patent
Ikeda et al.

(10) Patent No.: US 7,186,532 B2
(45) Date of Patent: Mar. 6, 2007

(54) PROCESS FOR PRODUCING D-SERINE

(75) Inventors: Hajime Ikeda, Tokyo (JP); Yoshiyuki Yonetani, Tokyo (JP); Shin-ichi Hashimoto, Yamaguchi (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/415,107

(22) PCT Filed: Oct. 29, 2001

(86) PCT No.: PCT/JP01/09482

§ 371 (c)(1),
(2), (4) Date: Sep. 3, 2003

(87) PCT Pub. No.: WO02/36803

PCT Pub. Date: May 10, 2002

(65) Prior Publication Data

US 2004/0072308 A1    Apr. 15, 2004

(51) Int. Cl.
| | |
|---|---|
| C12P 13/06 | (2006.01) |
| C12P 13/04 | (2006.01) |
| C12N 9/88 | (2006.01) |
| C12N 15/70 | (2006.01) |
| C12N 1/21 | (2006.01) |
| C12N 5/02 | (2006.01) |
| C07H 21/04 | (2006.01) |

(52) U.S. Cl. ................ 435/116; 435/106; 435/325; 435/232; 435/320.1; 435/252.33; 536/23.2

(58) Field of Classification Search ................ 435/116, 435/232, 320.1, 325, 252.3, 252.33; 536/23.2; 530/350
See application file for complete search history.

(56) References Cited

FOREIGN PATENT DOCUMENTS

| | | |
|---|---|---|
| JP | 5-091895 | 4/1993 |
| WO | 98/14602 | 4/1998 |

OTHER PUBLICATIONS

Witkowski et al., Biochemistry 38:11643-11650, 1999.*
Broun et al., Science 282:1315-1317, 1998.*
Seffernick et al., J. Bacteriol. 183(8):2405-2410, 2001.*
Hongsheng Su et al., "L-Serine Degradation in *Escherichia coli* K-12: Cloning and Sequencing of the *sdaA* Gene", Journal of Bacteriology, vol. 171, No. 9, pp. 5095-5102, (1989).
ZhongQi Shao et al., "Sequencing and Characterization of the *sdaB* Gene from *Escherichia coli* K-12", Eur. J. Biochem., vol. 212, pp. 777-784 (1993).
E.B. Newman et al., "In Vitro and In Vivo Activation of L-Serine Deaminase in *Escherichia coli* K-12", Journal of Bacteriology, vol. 162, No. 3, pp. 1270-1275 (1985).
Frederic R. Bloom et al., "Positive Control in the D-Serine Deaminase System of *Escherichia coli* K-12", Journal of Bacteriology, vol. 121, No. 3, pp. 1092-1101 (1975).
English language abstract of JP 5-091895.
Shao et al., "Sequencing and characterization of the sdaB gene from *Escherichia coli* K-12", European Journal of Biochemistry, vol. 212, No. 3, pp. 777-784 (1993).

* cited by examiner

*Primary Examiner*—Ponnathapu Achutamurthy
*Assistant Examiner*—Iqbal Chowdhury
(74) *Attorney, Agent, or Firm*—Greenblum & Bernstein, P.L.C.

(57) ABSTRACT

The present invention relates to: a process for producing D-serine wherein a microbial cell which is modified to have a higher L-serine deaminase activity than *Escherichia coli* DH5α strain, a culture of said cell, or a processed product thereof is brought into contact with DL-serine in a DL-serine-containing medium to decompose L-serine, and the remaining D-serine is recovered from the medium; and a microorganism used for this production process. D-serine is a useful compound as a synthetic intermediate for useful medicaments such as D-cycloserine.

7 Claims, No Drawings

PROCESS FOR PRODUCING D-SERINE

TECHNICAL FIELD

The present invention relates to: a process for producing D-serine wherein a microbial cell which is modified to have a higher L-serine deaminase activity than *Escherichia coli* DH5α strain, a culture of said cell, or a processed product thereof is brought into contact with DL-serine in a DL-serine-containing medium to decompose L-serine, and the remaining D-serine is recovered from the medium; and a microorganism used for this production process. D-serine is a useful compound as a synthetic intermediate for useful medicaments such as D-cycloserine.

BACKGROUND ART

The following production processes for D-serine are known:

(i) a process wherein DL-hydroxymethyl hydantoin is converted into N-carbamyl-D-serine with the aid of a microorganism, followed by hydrolysis to obtain D-serine (Japanese Published Unexamined Patent Application No. 61-152291);

(ii) a process wherein a microorganism belonging to the genus *Candida, Torulopsis, Cryptococcus, Saccharomycopsis, Hansenula, Escherichia, Klebsiella, Providencia, Microbacteriun,* or *Serratia* and assimilating L-serine but not substantially assimilating D-serine is cultured in a DL-serine-containing medium, and D-serine is isolated from the culture (Japanese Published Unexamined Patent Application No. 64-2594); and (iii) a process wherein a microorganism having a tyrosinase activity is allowed to act on a reaction solution containing DL-serine and phenol to convert L-serine into L-tyrosine, and remaining D-serine is recovered (Japanese Published Unexamined Patent Application No. 5-91895).

All of these production processes have problems when used as methods for industrially producing D-serine. Specifically, in process (i), the yield of N-carbamyl-D-serine from DL-hydroxymethyl hydantoin is as low as 40%, and a large amount of cells of a microorganism is required as catalyst In process (ii), L-serine remains after the reaction, and this requires the resolution of DL-serine. In process (iii), the substrate concentration is as low as 1%, and harmful phenol is required in the reaction. These problems complicate the industrial application of these production processes.

*Eschericia coli* is known to have an L-serine deaminase activity for decomposing L-serine into ammonia, pyruvic acid and water [J. Bacteriol., 171, 5095–5102 (1989), Eur. J. Biochem., 212, 777–784 (1993)]. However, it is reported that the enzyme extracted from *Escherichia coli* needs complex conditions such as the addition of iron and a reducing agent at the time of reaction [J. Bacteriol., 162, 1270–1275 (1985)], and the use of the purified enzyme for D-serine production is not practical.

*Escherichia coli* is also known to have a D-serine deaminase activity for decomposing D-serine [J. Bacteriol., 121, 1092–1101 (1975)]. Accordingly, D-serine produced using *Escherichia coli* from DL-serine with the aid of L-serine deaminase is disadvantageously decomposed by the D-serine deaminase, and this sometimes deteriorates the production efficiency.

Thus, a process for efficiently producing D-serine from DL-serine is not yet established in the conventionally known methods.

DISCLOSURE OF THE INVENTION

An object of the present invention is to provide an industrially useful process for producing D-serine.

The present inventors have found that, surprisingly, L-serine can be rapidly decomposed and eliminated to a level below the lower detection limit without substantially reducing D-serine by bringing *Escherichia coli* that is modified to have a higher L-serine deaminase activity than *Escherichia coli* DH5α strain or a processed product thereof into contact with DL-serine without extracting or purifying L-serine deaminase from said *Escherichia coli*. They also have found that this enables the industrial production of D-serine. This led to the completion of the present invention.

The present invention relates to the following (1) to (12).

(1) A process for producing D-serine, which comprises bringing a cell of a microorganism which is modified to have a higher L-serine deaminase activity than *Escherichia coli* DH5α strain, a culture of said cell, or a processed product thereof into contact with DL-serine in a DL-serine-containing medium to decompose L-serine, and recovering the remaining D-serine from the medium.

(2) A process for producing D-serine, which comprises culturing a microorganism which is modified to have a higher L-serine deaminase activity than *Escherichia coli* DH5α strain in a DL-serine-containing medium to decompose L-serine, and recovering the remaining D-serine from the culture.

(3) The process for producing D-serine according to (1) or (2) above, wherein the modified microorganism is a mutant microorganism obtainable by mutating a microorganism having a L-serine deaminase activity.

(4) The process for producing D-serine according to (1) or (2) above, wherein the modified microorganism is a transformant obtainable by introducing an L-serine deaminase gene into a microorganism.

(5) The process for producing D-serine according to any one of (1) to (4) above, wherein the L-serine deaminase activity of the modified microorganism is twice or higher compared to that of *Escherichia coli* DH5α strain.

(6) The process for producing D-serine according to any one of (1) to (4) above, wherein the L-serine deaminase activity of the modified microorganism is five times or higher compared to that of *Escherichia coli* DH5α strain.

(7) The process for producing D-serine according to (4) above, wherein the L-serine deaminase gene is the sdaA or sdaB gene derived from *Escherichia coli*.

(8) The process for producing D-serine according to any one of (1) to (7) above, wherein the modified microorganism is a microorganism belonging to *Escherichia coli*.

(9) The process for producing D-serine according to any one of (1) to (8) above, wherein the modified microorganism is selected from the group consisting of *Escherichia coli* DH5a/pHIB, *Escherichia coli* NM522/pHIA1, *Escherichia coli* MM294/pHIA1, *Escherichia coli* MM294/pHIA2, *Escherichia coli* MM294/pHIB, and *Escherichia coli* ME5386/pHIA2.

(10) The process for producing D-serine according to any one of (1) to (9) above, wherein the modified microorganism has low or no D-serine deaminase activity.

(11) A microorganism, which belongs to *Escherichia coli* and is modified to have a higher L-serine deaminase activity than *Escherichia coli* DH5α strain.

(12) The microorganism according to (11) above, which is selected from the group consisting of *Escherichia coli* DH5a/pHIB, *Escherichia coli* NM522/pHIA1, *Escherichia* coli MM294/pHIA1, *Escherichia coli* MM294/pHIA2, *Escherichia coli* MM294/pHIB, and *Escherichia coli* ME5386/pHIA2.

The present invention is hereinafter described in detail.

1. Obtaining of a Microorganism that is Modified to have a Higher L-Serine Deaminase Activity than *Escherichia coli* DH5α Strain A microorganism that is modified to have a higher L-serine deaminase activity than *Escherichia coli* DH5α strain (manufactured by Toyobo Co., Ltd., the same shall apply hereinafter) used in the present invention (this is hereinafter abbreviated as a "modified microorganism") can be obtained in the manner described below.

A microorganism to be modified (hereinafter it is referred to as a "parent strain") may or may not have an L-serine deaminase activity.

When the parent strain has an L-serine deaminase activity, a modified microorganism can be obtained by the method described in (1) or (2) below.

When the parent strain has no L-serine deaminase activity, a modified microorganism can be obtained by the method described in (2) below.

According to the production method of the present invention, D-serine can be produced at high yield. Thus, even if D-serine is decomposed by D-serine deaminase, D-serine can be still produced at high yield.

Thus, the parent strain may or may not have D-serine deaminase activity.

(1) Obtaining by Mutation

The modified microorganism can be obtained from a microorganism obtained by mutagenizing the parent strain (hereinafter abbreviated as "mutated microorganism").

Mutation can be applied by any commonly employed methods, and examples thereof include a method using a mutagen and an ultraviolet irradiation method.

Examples of a preferred method using a mutagen include a method using N-methyl-N'-nitro-N-nitrosoguanidine (NTG) (Biseibutsu Jikken Manual (Experimental Manual on Microorganism), p. 131, 1986, Kodansha Scientifics).

The mutated microorganism is cultured in accordance with the method described below, and a microorganism having an increased IL-serine deaminase activity compared to that of *Escherichia coli* DH5α strain is selected, thereby obtaining a modified microorganism.

L-serine deaminase activity that is at least increased compared to that of *Escherichia coli* DH5α strain is sufficient. The activity is preferably increased by two-fold or more, and more preferably by 5-fold or more.

The L-serine deaminase activity can be assayed in accordance with the method described in, for example, Meth. Enzymol., 17B, 346 (1971) and Meth. Enzymol., 17B, 351 (1971). Also, the method described below can be used as a simplified method.

Specifically, after the modified microorganism is brought into contact with DL-serine, the amount of L-serine remaining in the reaction solution is measured to calculate the amount of L-serine decreased per unit time. Thus, the activity can be assayed.

For example, the amount of L-serine decreased from the beginning of the reaction to a certain point during the reaction, i.e., the amount decomposed, is measured, and the obtained value of the amount decomposed is divided by the reaction time. Thus, the amount of L-serine decomposed per unit time is calculated, and the obtained value can be regarded as the L-serine deaminase activity.

More specifically, the obtained mutated microorganism is cultured at 30° C. for 1 day, and the resulting culture is centrifuged to obtain cells. Any medium can be used for culturing as long as the mutated microorganism can be cultured. The cells are suspended in a 50 mmol/L phosphate buffer (pH 7.5), and the cells obtained by centrifugation (the weight of wet microorganisms: about 2 g) are used in the reaction.

The obtained cells are suspended in a phosphate buffer (pH 7.5) containing 50 g/L DL-serine, and a reaction is carried out at 37° C. for 10 to 22 hours. After the completion of the reaction, the concentrations of D-serine and L-serine are quantified by HPLC to calculate the content in the buffer.

(2) Method Using Gene Recombination

A modified microorganism can be obtained by obtaining an L-serine deaminase gene and introducing the gene into a host cell according to the method described below.

(a) Obtaining of L-Serine Deaminase Gene

The L-serine deaminase gene can be cloned based on the known nucleotide sequences of L-serine deaminase gene of *Escherichia coli* [J. Bacteriol., 171, 5095–5102 (1989), Eur. J. Biochem., 212, 777–784 (1993)]. A method for obtaining sdaA and sdaB, i.e., the L-serine deaminase genes of *Escherichia coli*, is described below as an example. However, a source for obtaining the L-serine deaminase gene is not limited to *Escherichia coli*, as long as the microorganism has the L-serine deaminase activity.

For example, sdaA and sdaB can be obtained in the following manner.

*Escherichia coli*, for example, *Escherichia coli* W3110 strain, is cultured in accordance with a conventional method in a medium that is suitable for culturing *Escherichia coli*, such as LB medium [a medium containing 10 g of Bactotrypton (manufactured by Difco), 5 g of yeast extract (manufactured by Difco), and 5 g of NaCl in 1 liter of water (pH 7.2)]. After culturing, microorganisms are obtained from the culture by centrifugation.

Chromosomal DNA is isolated from the obtained microorganisms in accordance with a conventional method [for example, as described in Sambrook, J. et al., Molecular Cloning: A Laboratory Manual, Second Edition, Cold Spring Harbor Laboratory Press (2001), hereinafter it is referred to as "Molecular Cloning, Vol. 3"].

Using the information on nucleotide sequences of the L-serine deaminase gene described in J. Bacteriol., 171, 5095–5102 (1989) or Eur. J. Biochem., 212, 777–784 (1993), a sense primer and an antisense primer comprising a nucleotide sequence that corresponds to the sdaA or sdaB gene are synthesized using a DNA synthesizer.

DNA fragments are amplified by PCR using the obtained sense primer, antisense primer, and chromosomal DNA. In order to introduce the amplified DNA fragments into a plasmid, a suitable restriction enzyme site, such as BamHI is preferably added to the 5' end of the sense and antisense primers.

Examples of combinations of the sense primer and the antisense primer include a combination of two primers having the nucleotide sequences as shown in SEQ ID NOS: 1 and 2, a combination of two primers having the nucleotide sequences as shown in SEQ ID NOS: 1 and 3 (for sdaA), and a combination of two primers having the nucleotide sequences as shown in SEQ ID NOS: 4 and 5 (for sdaB).

PCR is carried out on DNA Thermal Cycler (manufactured by Perkin Elmer Japan) using chromosomal DNA as a template and using these primers and TaKaRa LA-PCR TM Kit Ver. 2 (manufactured by Takara Shuzo Co., Ltd.) or Expand TM High-Fidelity PCR System (manufactured by Boehringer Mannheim).

Examples of PCR conditions include: when a 2 kb or smaller DNA fragment is amplified, repeating 30 cycles of a reaction process comprising reaction at 94° C. for 30 seconds, 55° C. for 30 seconds to 1 minute, and 72° C. for 2 minutes, followed by a reaction at 72° C. for 7 minutes; and when a DNA fragment exceeding 2 kb is amplified, repeating 30 cycles of a reaction process comprising reaction at 98° C. for 20 seconds and 680C for 3 minutes, followed by a reaction at 72° C. for 7 minutes.

The DNA fragment amplified by PCR and a vector that is replicable in *Escherichia coli* are cleaved using restriction enzymes at the same restriction enzyme sites as with the primers. Thereafter, agarose gel electrophoresis, sucrose density gradient ultracentrifugation, and the like are carried out to collect DNA fragments.

The collected DNA fragments are used to prepare a cloning vector in accordance with a conventional method such as a method described in, for example, Molecular Cloning, Vol. 2, Current Protocols in Molecular Biology, Supplement 1–38, John Wiley & Sons (1987–1997) (hereinafter abbreviated to "Current Protocols in Molecular Biology, Supplement"), and DNA Cloning 1: Core Techniques, A Practical Approach, Second Edition, Oxford University Press (1995), or using a commerchially available kit, such as SuperScript Plasmid System for cDNA Synthesis and Plasmid Cloning (manufactured by Life Techcologies) or ZAP-cDNA Synthesis Kit (manufactured by Stratagene), and then *Escherichia coli*, for example, *Escherichia coli* DH5α strain (manufactured by Toyobo Co., Ltd.) is transformed with the obtained cloning vector.

Any vector such as a phage vector or plasmid vector can be used as a cloning vector for transforming *Escherichia coli*, as long as it is autonomously replicable in *Escherichia coli* K12 strain. An expression vector for *Escherichia coli* can also be used as a cloning vector. Specific examples thereof include ZAP Express (Stratagene, Strategies, 5, 58 (1992)), pBluescript II SK(+) (Nucleic Acids Research, 17, 9494 (1989)), Lambda ZAP II (manufactured by Stratagene), λgt10, λgt11 (DNA Cloning, A Practical Approach, 1, 49 (1985)), λTriplEx (manufactured by Clontech), λExCell (manufactured by Pharmachia), pT7T318U (manufactured by Pharmachia), pcD2 (Mol. Cell. Biol., 3, 280 (1983)), pMW218 (manufactured by Wako Pure Chemical Industries, Ltd.), pUC 118, pSTV28 (manufactured by Takara Shuzo Co., Ltd.), pEG400 (J. Bacteriol., 172, 2392 (1990)), pHMV1520 (manufactured by MoBiTec), and pQE-30 (manufactured by QIAGEN).

A plasmid containing a gene of interest can be obtained from the obtained transformant in accordance with a conventional technique, for example, the method described in Molecular Cloning, Vol. 3, Current Protocols in Molecular Biology, Supplement, and DNA Cloning 1: Core Techniques, A Practical Approach, Second Edition, Oxford University Press (1995), and the like.

In accordance with the aforementioned methods, a plasmid which comprises a gene encoding a protein having an L-serine deaminase activity can be obtained. Examples of the plasmid include pHIA1, pHIA2, and pHIB exemplified in Examples below.

With a similar method, the L-serine deaminase gene can be obtained from a living organism having a known nucleotide sequence of genomic DNA. Also, a plasmid which comprises DNA encoding a protein having an L-serine deaminase activity can be obtained from a living organism having an unknown nucleotide sequence of genomic DNA by producing a chromosomal DNA library using a suitable vector and using *Escherichia coli* as a host, and investigating the L-serine deaminase activity for each strain in the library.

(b) Expression Method of L-serine Deaminase Gene

In order to express DNA encoding L-serine deaminase obtained as above in a host cell, DNA encoding L-serine deaminase of interest is first cleaved with restriction enzymes or deoxyribonucleases to prepare a DNA fragment of a suitable length containing a coding region. Subsequently, the DNA fragment is inserted downstream of a promoter in an expression vector, and the expression vector into which the DNA has been inserted is then introduced into a host cell that is compatible with the expression vector.

Any cells such as a procaryotic cell, yeast, animal cell, or insect cell can be used as a host cell, as long as the gene of interest can be expressed therein.

Examples of usable expression vectors include those which are autonomously replicable or capable of being incorporated into chromosome in the host cell and comprise a promoter at a position to which the DNA of interest can be transcribed.

When procaryotic organisms such as bacteria or Actinomycetes are used as host cells, preferably, an expression vector for expressing the aforementioned DNA is autonomously replicable in the procaryotic organism and, at the same time, is a recombinant vector composed of a promoter, a ribosome binding sequence, the aforementioned DNA, and a transcription termination sequence. A gene which controls a promoter may also be contained.

Examples of expression vectors include pBTrp2, pBTac1, pBTac2 (manufactured by Boehringer Mannheim), pKK233-2 (manufactured by Pharmachia), pSE280 (manufactured by Invitrogen), pGEMEX-1 (manufactured by Promega), pQE-8 (manufactured by QIAGEN), pQE-30 (manufactured by QIAGEN), pKYP10 (Japanese Published Unexamined Patent Application No. 58-110600), pKYP200 [Agric. Biol. Chenm, 48, 669 (1984)], pLSA1 [Agric. Biol. Chem., 53, 277 (1989)], pGEL1 [Proc. Natl. Acad. Sci. USA, 82, 4306 (1985)], pBluescriptII SK+, pBluescriptII SK (−) (manufactured by Stratagene), pTrS30 (FERM BP-5407), pTrS32 (FERM BP-5408), pGEX (manufactured by Pharmachia), pET-3 (manufactured by Novagen), pTerm2 (U.S. Pat. Nos., 4,686,191, 4,939,094, 5,160,735), pSupex, pUB 110, pTP5, pC194, pUC18 [Gene, 33, 103 (1985) ], pUC19 [Gene, 33, 103 (1985)], pSTV28 (manufactured by Takara Shuzo Co., Ltd.), pSTV29 (manufactured by Takara Shuzo Co., Ltd.), pUC118 (manufactured by Takara Shuzo Co., Ltd.), pPA1 (Japanese Published Unexamined Patent Application No. 63-233798), pEG400 [J. Bacteriol., 172, 2392 (1990)], pQE-30 (manufactured by QIAGEN), PHY300 (manufactured by Takara Shuzo Co., Ltd.), and pHW1520 (manufactured by MoBiTec).

Any promoter can be used as long as it can be expressed in a host cell. Examples thereof include promoters derived from *Escherichia coli* or phage such as trp promoter ($P_{trp}$), lac promoter ($P_{lac}$), $P_L$ promoter, $P_R$ promoter, and $P_{SE}$ promoter, SPO1 promoter, SPO2 promoter, and penP promoter. Also, a promoter ($P_{trp} \times 2$) in which two $P_{trp}$ are connected in series or artificially designed and modified promoters such as tac promoter, letI promoter, and lacT7 promoter can be used. Further, xylA promoter for expression in a microorganism belonging to the genus *Bacillus*, P54-1 promoter for expression in a microorganism belonging to the genus *Coryncbacterium*, and the like can be used.

Any sequence may be employed as a ribosome binding sequence as long as it can be expressed in a host cell. A plasmid in which the distance between the Shine-Dalgamo sequence and an initiation codon is regulated to a suitable distance (e.g., 6 to 18 nucleotides) is preferably used.

For the purpose of efficient transcription and translation, a fusion protein which is prepared by fusing a protein having L-serine deaminase activity and having its N terminus or a portion thereof deleted with the N-terminal portion of a protein coded by an expression vector, may be expressed.

A transcription termination sequence is not always necessary for the expression of the protein of interest, but preferably, a transcription termination sequence is located at an immediately downstream of the structural gene.

Examples of host cells include microorganisms belonging to the genus *Escherichia, Corynebacteliun, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Phorwidiun, Rhodobacter, Rhodopseudomonas, Rhodospirillun, Scenedesmus, Streptomyces, Synnechococcus,* or *Zymomonas*.

Specific examples thereof include *Escherichia coli, Bacillus subtilis, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia marcescens, Agrobacterium rhizogenes, Arthrobacter aurescens, Arthrobacter nicotianae, Arthrobacter sulfureus, Arthrobacter ureafaciens, Erwinia carotovora, Erwinia herbicola, Methylobacterium extorquens, Phormidium* sp., *Rhodobacter sphaeroides, Rhodospirillum rubrum, Streptomyces aureofaciens, Streptomyces griseus,* and *Zymomonas mobilis*.

More specific examples include *Escherichia coli* XL1-Blue (manufactured by Stratagene), *Escherichia coli* XL2-Blue (manufactured by Stratagene), *Escherichia coli* DH1 (Molecular Cloning, Vol. 2, p. 505), *Escherichia coli* DH5 a (manufactured by Toyobo Co., Ltd.), *Escherichia coli* MC1000 [Mol. Biol., 138, 179–207 (1980)], *Escherichia coli* W1485 (ATCC12435), *Escherichia coli* JM109 (manufactured by Stratagene), *Escherichia coli* HB101 (manufactured by Toyobo Co., Ltd.), *Escherichia coli* W3110 (ATCC14948), *Escherichia coli* NM522 (manufactured by Stratagene), *Bacillus subtilis* ATCC33712, *Bacillus* sp, FERM BP-6030, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratia marcescens* ATCC13880, *Agrobacterium rhizogenes* ATCC11325, *Arthrobacter aurescens* ATCC13344, *Arthrobacter nicotianae* ATCC15236, *Arthrobacter sulfureus* ATCC19098, *Arthrobacter ureafaciens* ATCC7562, *Erwinia carotovora* ATCC15390, *Erwinia herbicola* ATCC21434, *Methylobacterium extorquens* DSM1337, *Phormidium* sp. ATCC29409, *Rhodobacter sphaeroides* ATCC21286, *Rhodospirillum rubrum* ATCC11170, *Streptomyces aureofaciens* ATCC10762, *Streptomyces griseus* ATCC10137, and *Zymomonas mobilis* ATCC10988.

Examples of a microorganism having low or no D-serine deaminase activity include *Escherichia coli* ME5386 (available from National Institute of Genetics).

Any method can be used to introduce a recombinant vector into a host cell as long as the method is for introducing DNA into a host cell. Examples thereof include a method using calcium ion [Proc. Natl. Acad. Sci. USA, 69, 2110 (1972)], the protoplast method (Japanese Published Unexamined Patent Application No. 63-248394), the electroporation, and a method described in Gene, 17, 107 (1982) or Molecular & General Genetics, 168, 111 (1979).

When yeast is used as a host cell, examples of expression vectors include YEp13 (ATCC37115), YEp24 (ATCC37051), YCp50(ATCC37419), pHS19, and pHS15.

Any promoter can be used as long as it can be expressed in yeast, and examples thereof include PHO5 promoter, PGK promoter, GAP promoter, ADH promoter, gal 1 promoter, gal 10 promoter, heat shock protein promoter, MFa1 promoter, and CUP1 promoter.

Examples of host cells include microorganisms belonging to the genus *Saccharomyces, Schizosaccharomyces, Kluyveromyces, Trichosporon, Schwanniomyces, Pichia,* or *Candida*, and specific examples thereof include *Saccharomyces cerevisiae, Schizosaccharomyces pombe, Kluyveromyces lactis, Trichosporon pullulans, Schwanniomyces alluvius,* and *Candida utilis*.

Any method can be used for introducing a recombinant vector as long as the method is for introducing DNA into yeast Examples thereof include the electroporation [Methods in Enzymol., 194, 182 (1990)], the spheroplast method [Proc. Natl. Acad. Sci. USA, 75, 1929 (1978)], the lithium acetate method [J. Bacteriol., 153, 163 (1983)], and a method described in Proc. Natl. Acad. Sci. USA, 75, 1929 (1978).

When an animal cell is used as a host cell, examples of an expression vector include pcDNAL pcDM8 (manufactured by Funakoshi), pAGE107 [Japanese Published Unexamined Patent Application No. 3-22979; Cytotechnology, 3, 133, (1990)], pAS3-3 (Japanese Published Unexamined Patent Application No. 2-227075), pCDM8 [Nature, 329, 840, (1987)], pcDNAI/Amp (manufactured by Invitrogen), pREP4 (manufactured by Invitrogen), pAGE103 [J. Biochem., 101 1307 (1987)], and pAGE210.

Any promoter can be used as long as it can be expressed in an animal cell, and examples thereof include Cytomegalovirus (human CMV) immediate early (IE) gene promoter, SV40 early promoter, retrovirus promoter, metallothionein promoter, heat shock promoter, and SRα promoter. Human CMV IE gene enhancer may be used in combination with a promoter.

Examples of host cells include Namalwa cell, HBT5637 (Japanese Published Unexamined Patent Application No. 63-000299), COS1 cell, COS7 cell, and CHO cell.

Any method can be used to introduce a recombinant vector into an animal cell as long as the method is for introducing DNA into an animal cell, and examples thereof include the electroporation [Cytotechnology, 3, 133 (1990)], the calcium phosphate method (Japanese Published Unexamined Patent Application No. 2-227075), the lipofection method [Proc. Natl. Acad. Sci., USA, 84, 7413 (1987)], and a method described in Virology, 52, 456 (1973). A transformant can be obtained and cultured in accordance with the method described in Japanese Published Unexamined Patent Application No. 2-227075 or 2-257891.

When an insect cell is used as a host cell, a protein can be expressed in accordance with the method described in, for example, Baculovirus Expression Vectors, A Laboratory Manual, W. H. Freeman and Company, New York (1992), Current Protocols in Molecular Biology, Supplement, and Bio/Technology, 6, 47 (1988). Specifically, a recombinant gene introducing vector and a baculovirus are introduced together into the insect cell, a recombinant virus is obtained in a culture supernatant of the insect cell, and the insect cell is then infected with the recombinant virus, thereby expressing a protein.

Examples of gene introducing vectors that are used in the above method include pVL1392, pVL1393, and pBlueBacIII (manufactured by Invitrogen).

Examples of usable baculovirus include the *Autographa californica* nuclear polyhedrosis virus that infects an insect belonging to the *Mamestra*.

Examples of usable insect cells include ovarian cells of *Spodoptera frugiperda*, Sf9 and Sf21 (Baculovirus Expression Vectors, A Laboratory Manual, W. H. Freeman and Company, New York, 1992), and an ovarian cell of *Trichoplusia ni*, High5 (manufactured by Invitrogen).

Examples of methods for introducing the recombinant gene introducing vector and the baculovirus together into the insect cell for preparing the recombinant virus include the calcium phosphate method (Japanese Published Unexamined Patent Application No. 2-227075) and the lipofection method [Proc. Natl. Acad. Sci. USA, 84, 7413(1987)].

As methods other than direct expression, the gene can be expressed by secretory production, fusion protein expression and the like in accordance with a method described in, for example, Molecular Cloning, Vol. 2.

When the gene is expressed in yeast, an animal cell, or an insect cell, a protein having a sugar or sugar chain added can be obtained.

2. Culturing of Modified Microorganism

The modified microorganism of the present invention which is obtained in 1 above can be cultured in a medium in accordance with a conventional method that is used for culturing host cells. When the modified microorganism of the present invention is a procaryotic microorganism such as *Escherichia coli* or a eucaryotic microorganism such as yeast, a medium for culturing these microorganisms may be natural or synthetic as long as it contains carbon sources, nitrogen sources, inorganic salts, and the like which are assimilable by the microorganism and is a medium suitable for efficient culturing of the transformant The carbon sources may be those assimilable by the modified microorganisms. Examples thereof include: carbohydrates such as glucose, fructose, sucrose, molasses comprising them, and starch or starch hydrolysate; organic acids such as acetic acid and propionic acid; and alcohols such as ethanol and propanol.

Examples of usable nitrogen sources include: ammonia; ammonium salts of various inorganic or organic acids such as ammonium chloride, ammonium sulfate, ammonium acetate, and ammonium phosphate; other nitrogen-containing compounds; peptone; meat extract; yeast extract; corn steep liquor; casein hydrolysate; soybean cake; hydrolysate of soybean cake; and various fermentation microorganisms and digests thereof.

Examples of usable inorganic salts include: monopotassium phosphate, dipotassium phosphate, magnesium phosphate, magnesium sulfate, sodium chloride, iron(I) sulfate, manganese sulfate, copper sulfate, and calcium carbonate.

Culturing is carried out under aerobic conditions such as shaking culturing or submerged spinner culture under aeration. Culture temperature is preferably 15 to 50° C., and culture time is generally 16 hours to 7 days. During the culturing, the pH is maintained to 3.0 to 9.0. The pH is adjusted with an inorganic or organic acid, an alkali solution, urea, calcium carbonate, ammonia, or the like.

During the culturing, an antibiotic such as ampicillin or tetracycline may be added to the medium, if necessary.

When a microorganism transformed with an expression vector using an inducible promoter is cultured, an inducer may be added to the medium, if necessary. For example, when a microorganism transformed with an expression vector using Lac promoter is cultured, isopropyl-β-D-thiogalactopyranoside (EITG) or the like may be added to the medium. When a microorganism transformed with an expression vector using trp promoter is cultured, indoleacrylic acid (IAA) or the like may be added to the mediurm When a microorganism transformed with an expression vector containing xyla promoter is cultured, xylose may be added to the medium.

When the modified microorganism of the present invention is an animal cell, examples of a usable medium for culturing the modified animal cell include commonly used RPMI 1640 medium [The Journal of the American Medical Asschiation, 199, 519 (1967)], Eagle's MEM medium [Science, 122, 501 (1952)], DMEM medium [Virology, 8, 396 (1959)], 199 medium [Proceeding of the Society for the Biological Medicine, 73, 1(1950)], and a medium prepared by adding fetal bovine serum to the above media.

Usually, culturing is carried out at pH 6 to 8 at 30 to 40° C. in the presence of 5% $CO_2$ for 1 to 7 days.

During the culturing, an antibiotic such as kanamycin or penicillin may be added to the medium, if necessary.

When the modified microorganism of the present invention is an insect cell, examples of a usable medium for culturing the modified insect cell include commonly used TNM-FH medium [PharMingen], Sf-900 II SFM medium (manufactured by GIBCO BRL), ExCell 400 and ExCell 405 [manufactured by JRH Biosciences], and Grace's Insect Medium [Grace, T. C. C., Nature, 195, 788 (1962)].

Usually, culturing is carried out at pH 6 to 7 at 25 to 30° C. for 1 to 5 days.

During the culturing, an antibiotic such as gentamicin may be added to the medium, if necessary.

3. Production of D-Serine

The modified microorganism is brought into contact with DL-serine in a DL-serine-containing medium to decompose L-serine, and the remaining D-serine is recovered from the medium. Thus, D-serine can be produced.

The L-serine deaminase activity in the transformant or mutated microorganism should be enhanced compared to that in *Escherichia coli* DH5α strain. It is sufficient if the level of L-serine deaminase activity is higher than that of *Escherichia coli* DH5α strain, and the activity level is preferably twice or higher, and more preferably 5 times or higher.

The production efficiency for D-serine can be increased with the use of a strain having low or no D-serine deaminase activity.

The L-serine deaminase activity is assayed as described in 1. (1) above.

Production of D-serine using the above microorganism can be carried out in the following manner.

Namely, the cell of a modified microorganism obtained by the above method, the cultured product of the cell, or a processed product thereof (hereinafter referred to as "enzyme source") are brought into contact with DL-serine in a medium.

Examples of cells or processed products of the cells include: dried cells; processed cells such as freeze-dried cells, surfactant-processed cells, enzyme-processed cells, ultrasonically disrupted cells, mechanically ground cells, and solvent-processed cells; processed culture products such as concentrated and dried culture products; protein fraction of cells; immobilized products of cells and processed cells; and purified enzymes obtained from cells.

The modified microorganism is bought into contact with DL-serine by previously adding DL-serine in a medium for culturing the modified microorganism or by adding DL-serine during the culturing. The enzyme source obtained by culturing the modified microorganism may be added to a DL-serine-containing medium.

When DL-serine is added to a medium for culturing the modified microorganism, DL-serine is added in an amount of 1 to 300 mg, preferably 30 to 100 mg, per ml of medium at the time of initiation or during the culturing. Culturing can be conducted under conditions described in (2) above.

When the enzyme source obtained from the modified microorganism is brought into contact with DL-serine in a medium, the amount of the enzyme source varies depending on the specific activity of the enzyme source, and the like. For example, when the cell of the modified microorganism is used as an enzyme source, 5 to 1,000 mg, preferably 10 to 400 mg, of wet cells is added per mg of DL-serine.

The contacting reaction is preferably carried out at 20 to 50° C., and particularly preferably at 25 to 37° C. The reaction time varies depending on, for example, the amount and specific activity of an enzyme source used, and it is generally 2 to 150 hours, and preferably 5 to 60 hours.

As a medium, water or aqueous medium, an organic solvent, or a mixed solution of water or aqueous medium and an organic solvent is used. Examples of a usable aqueous medium include phosphate buffer, HEPES (N-2-hydroxyethylpiperazine-N-ethane sulfonic acid) buffer, and tris[tris(hydroxymethyl)aminomethane] hydrochloride buffer. Any organic solvent can be used unless it inhibits the reaction. Examples of a usable organic solvent include acetone, ethyl acetate, dimethyl sulfoxide, xylene, methyl alcohol, ethyl alcohol, and butanol.

When DL-serine is added to a medium, the DL-serine may be dissolved in water or an aqueous medium, an organic solvent, or a mixed solution of the water or aqueous medium and organic solvent, which can dissolve DL-serine, and the dissolved DL-serine may be then added in a medium. Alternatively, DL-serine may be added in the state of powder or granule.

D-serine can be recovered from the reaction medium in accordance with methods commonly used in the field of organic synthetic chemistry, such as extraction using organic solvent, crystallization, thin-layer chromatography, or high-performance liquid chromatography.

The D-serine obtained by the present invention can be confirmed or quantified by any suitable method. Examples thereof include $^{13}$C-NMR spectrum, $^1$H-NMR spectrum, mass spectrum, and high-performance liquid chromatography (HPLC).

Examples of the present invention are presented below, although the present invention is not limited to these examples.

BEST MODE FOR CARRYING OUT THE INVENTION

EXAMPLE 1

1) Obtaining of L-Serine Deaminase Gene

*Escherichia coli* W3110 strain (ATCC14948) was inoculated on 10 mL of LB medium using a platinum loop and cultured at 30° C. overnight. After culturing, cells were obtained from the culture by centrifugation (3,000 rpm, 10 minutes). Chromosomal DNA was isolated and purified from the cells in accordance with a conventional technique (a method described in Molecular Cloning, Vol. 2).

Two primers having the nucleotide sequences as shown in SEQ ID NOS: 1 and 2 and two primers having the nucleotide sequences as shown in SEQ ID NOS: 1 and 3, each of which is a combination of a sense primer and an antisense primer, were synthesized using a DNA synthesizer based on the nucleotide sequence information of sdaA that is a gene encoding L-serine deaminase [J. Bacteriol., 171, 5095–5102 (1989)]. In the same manner as for sdaA, two primers having the nucleotide sequences as shown in SEQ ID NOS: 4 and 5 were synthesized using a DNA synthesizer based on the nucleotide sequence information of sdaB that is a gene encoding L-serine deaminase [Eur. J. Biochem., 212, 777–784 (1993)].

PCR was carried out on DNA Thermal Cycler (manufactured by Perkin Elmer Japan) using chromosomal DNA as a template, pfu polymerase cloned (manufactured by Stratagene), and pfu polymerase 10 × Reaction Buffer (standard buffer).

PCR was carried out by repeating 30 cycles of reaction at 94° C. for 30 seconds, at 55° C. for 30 seconds to 1 minute, and at 72° C. for 2 minutes, followed by a reaction at 72° C. for 7 minutes. The DNA fragments amplified by PCR were digested with restriction enzymes HindIII and BamHI. After the digestion, these DNA fragments digested with restriction enzymes were subjected to agarose gel electrophoresis to obtain DNA fragments digested with each restriction enzyme.

2) Preparation of Recombinant DNA

Vector plasmid pTrS30 having an ampicillin resistant gene and Trp promoter (extracted from FERM BP-5407 by a conventional technique) was digested with restriction enzymes HindIII and BamHI and subjected to agarose gel electrophoresis to obtain a HindIII-BamHI-treated pTrS30 fragment.

The HindIII-BamHI-trated DNA fragment obtained above and the HindIII-BamHI-treated pTrS30 fragment were mixed together and then ligated to each other to obtain a recombinant DNA.

The recombinant DNA was used to transform *Escherichia coli* DH5α strain (manufactured by Toyobo Co., Ltd.) by a conventional technique. The transformant was then spread on LB agar medium containing 100 µg/mL ampicillin [a medium containg 10 g of Bactotrypton (manufactured by Difco), 5 g of yeast extract (manufactured by Difco), and 5 g of NaCl in 1 liter of water, pH 7.2, agar content 1.5%] and cultured at 30° C. for 1 day.

Several colonies of the transformant grown on the medium were cultured in 10 mL of LB medium containing 100 µg/mL ampicillin at 30° C. for 1 day.

The obtained culture was centrifiged to obtain cells of the transformant. Plasmid was isolated from the cells by a conventional technique.

A HindIII-BamHI-treated DNA fragment (the DNA fragment obtained by PCR amplification of the combination of two primers having the nucleotide sequences as shown in SEQ ID NOS: 1 and 2) was ligated with the HindIII-BamHI-treated pTrS30 fragment to obtain a plasmid The obtained plasmid was designated as pHIA1. A HindIII-BamHI-treated DNA fragment (the DNA fragment obtained by PCR amplification of the combination of two primers having the nucleotide sequences as shown in SEQ ID NOS: 1 and 3) was ligated with the HindIII-BamHI-treated pTrS30 fragment to obtain a plasmid The obtained plasmid was designated as pHIA2. A HindIII-BamHI-treated DNA fragment (the DNA fragment obtained by PCR amplification of the combination of two primers having the nucleotide sequences as shown in SEQ ID NOS: 4 and 5) was ligated with the HindIII-BamHI-treated pTrS30 fragment to obtain a plasmid. The obtained plasmid was designated as pHIB1.

3) Preparation of Transfonmant

The thus obtained plasmids were introduced into *Escherichia coli* NM522 (Stratagene), *Escherichia coli* MM294 (ATCC33625), and *Escherichia coli* ME5386 strain, which is deficient in a D-serine deaminase activity (available from National Institute of Genetics), in accordance with a conventional technique.

Of these strains, *Escherichia coli* MM294/pHIA1 having pHIA1, *Escherichia coli* MM294/pHIA2 having pHIA2, and *Escherichia coli* MM294/pHIB having pHIB are respectively deposited under the accession numbers of FERM BP-7309, FERM BP-7310, and FERM BP-7311 under the Budapest Treaty at the International Patent Organism Depositary of the National Institute of Advanced Industrial Science and Technology, Chuo 6, 1-1-1 Higashi, Tsukuba, Ibaraki, Japan, which was formerly the National Institute of Bioscience and Human-Technology of the Agency of Industrial Science and Technology (METI), 1-3, Higashi 1 chome, Tsukuba, Ibaraki Japan, as of Sep. 28, 2000.

EXAMPLE 2

Expression of L-Serine Deaminase and Production of D-Serine

The thus obtained transformants and the *Escherichia coli* DH5α/pTrS30 strain having plasmid pTrS30 that does not contain L-serine deaminase gene were cultured in 100 mL of LB medium comprising 100 μg/mL ampicillin at 30° C. for 1 day. The obtained culture was centrifuged to obtain cells, and the obtained cells were resuspended in 50 mmol/L phosphate buffer (pH 7.5). The cells obtained by centrifugation (the weight of wet microorganisms: about 2 g) were used in the reaction.

The cells were suspended in a phosphate buffer (pH 7.5) containing 50 g/L DL-serine, and the reaction was carried out at 37° C. for 10 to 22 hours.

At the beginning, during, and after the reaction, the D-serine and L-serine contents in the reaction solution were quantified by HPLC.

The conditions for HPLC were as follows.
Column: CRAWNPAK CR(+) (Daicel Chemical Industries, Ltd.)
Fluidized bed: Aqueous solution of perchloric acid (pH 1.0)
Flow rate 0.2 mL/min
Column temperature: 2° C.
Detection was carried out by the post-column derivatization method using orthoaldehyde (OPA) [J. Chromatogr., 33–355 (1973)].

TABLE 1

| Strain | Plasmid | Reaction time (hour) | Total amount of L-serine decomposed (g/l) | D-serine content (g/l) | L-serine content (g/l) | Relative activity |
|---|---|---|---|---|---|---|
| DH5α | pTrS30 | 12 | 1.4 | | | 1.0 |
| | | 21 | | 23.2 | 21.5 | |
| DH5α | pHIB | 12 | 19.8 | | | 14.1 |
| | | 21 | | 24.9 | 0.0 | |
| NM522 | pHIA1 | 11 | 21.6 | | | 16.8 |
| | | 21 | | 23.7 | 0.0 | |
| ME5386 | pHIA2 | 12 | 23.5 | 25.6 | 0.0 | 16.8 |
| NM294 | pHIA1 | 10 | 20.3 | | | 17.4 |
| | | 22 | | | | |
| | pHIA2 | 10 | 19.4 | | | 16.6 |
| | | 22 | | 24.3 | 0.0 | |
| | pHIB | 10 | 8.5 | | | 7.3 |
| | | 22 | | | | |

The L-serine content in the reaction solution was determined 10, 11, or 12 hours after the intimidation of the reaction, and a difference from the L-serine content in the reaction solution at the beginning of the reaction was shown as the total amount of L-serine decomposed.

The value obtained by dividing the total amount of L-serine decomposed by the time passed since the initiation of the reaction (10, 11, or 12 hours) was shown as the L-serine deaminase activity, and the activity of each strain was shown as the relative activity when the L-serine deaminase activity of *Escherichia coli* DH5α/pTrS30 strain was regarded as 1.0.

As is apparent from Table 1, the L-serine content and the D-serine content 12 hours after the initiation of the reaction were measured for *Escherichia coli* ME5386/pHIA2 strain, those 21 hours after the initiation of the reaction were measured for *Escherichia coli* DH5a/pHIB strain and *Escherichia coli* NM522/pHIA1 strain, and those 22 hours after the initiation of the reaction were measured for *Escherichia coli* NM294/pHIA2 strain. The results showed that no L-serine remained, and that only D-serine remained in the reaction solution.

INDUSTRIAL APPLICABILITY

According to the present invention, D-serine that is useful as, for example, a synthetic intermediate for useful medicaments such as D-cycloserine, can be efficiently produced from DL-serine.

FREE TEXT OF SEQUENCE LISTINGS

SEQ ID NO: 1: synthetic DNA
SEQ ID NO: 2: synthetic DNA
SEQ ID NO: 3: synthetic DNA
SEQ ID NO: 4: synthetic DNA
SEQ ID NO: 5: synthetic DNA

The invention claimed is:

1. A process for producing D-serine, which comprises bringing a microorganism, or a processed product thereof comprising the *E. coli* sdaA or adaB gene product into contact with DL-serine in a DL-serine-containing medium to decompose L-serine, and recovering remaining D-serine from the medium, wherein said microorganism is obtained by a method comprising, introducing an *Escherichia coli* sdaA or sdaB gene into a microorganism to obtain a transformed microorganism, measuring the L-serine deaminase activity of the transformed microorganism, and selecting a transformed microorganism wherein the transformed microorganism has a higher L-serine deaminase activity than *Escherichia coli* DH5α strain.

2. The process for producing D-serine according to claim 1, wherein the L-serine deaminase activity of the transformed microorganism is twice or higher compared to that of *Escherichia coli* DH5α strain.

3. The process for producing D-serine according to claim 1, wherein the L-serine deaminase activity of the transformed microorganism is five times or higher compared to that of *Escherichia coli* DH5α strain.

4. The process for producing D-serine according to claim 1, wherein the transformed microorganism into a microorganism is a microorganism belonging to *Escherichia coli*.

5. The process for producing D-serine according to claim 1, wherein the microorganism is selected from the group consisting of *Esoharichia coli* DH5α/pHIB, *Escherichia coli* NM522/pHIA1, *Escherichia coli* MM294/pHIA1, *Escherichia coli* MM294/pHIA2, *Escherichia coli* MM294/pH 18, and *Escherichia coli* ME53866/pHIA2.

6. The process for producing D-serine according to claim 1, wherein the microorganism has low or no D-serine deaminase activity.

7. An *Escherichia coli* microorganism which is obtained by introducing an *Escherichia coli* sdaA or sdaB gene into the microorganism, which is selected from the group consisting of *Escherichia coli* DH5α/pHIB, *Escherichia coli* NM522/pHIA1, *Escherichia coli* MM294/pHIA1, *Escherichia coli* MM294/pHIA2, *Escherichia coli* MM294/pHIB, and *Escherichia coli* ME5386/pHIA2.

* * * * *

UNITED STATES PATENT AND TRADEMARK OFFICE
CERTIFICATE OF CORRECTION

PATENT NO. : 7,186,532 B2 Page 1 of 1
APPLICATION NO. : 10/415107
DATED : March 6, 2007
INVENTOR(S) : Ikeda et al.

It is certified that error appears in the above-identified patent and that said Letters Patent is hereby corrected as shown below:

At column 18, line 4 (claim 5 line 6), "MM294/pH 18" should be -- MM294/pHIB --.

Signed and Sealed this

Eighth Day of April, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
ccatcgataa gcttatgatt agtctattcg acatgtttaa gg                            42

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
cgcggatcct ggggaatatt acagcagac                                           29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
cgcggatcca gaagtattag tcacactgga c                                        31

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
cccaagctta tgattagcgt attcgatatt ttc                                      33

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
cgggatccat gagaaatcgg gaagaggc                                            28